US012752134B2

(12) United States Patent
Yoshizawa et al.

(10) Patent No.: US 12,752,134 B2
(45) Date of Patent: Oct. 6, 2026

(54) ULTRASONIC THERAPEUTIC APPARATUS

(71) Applicant: SONIRE THERAPEUTICS INC., Tokyo (JP)

(72) Inventors: Shin Yoshizawa, Miyagi (JP); Nao Yoshida, Miyagi (JP)

(73) Assignee: Sonire Therapeutics Inc., Tokyo (JP)

( * ) Notice: Subject to any disclaimer, the term of this patent is extended or adjusted under 35 U.S.C. 154(b) by 0 days.

(21) Appl. No.: 19/122,513

(22) PCT Filed: Dec. 12, 2023

(86) PCT No.: PCT/JP2023/044507
§ 371 (c)(1),
(2) Date: Apr. 18, 2025

(87) PCT Pub. No.: WO2025/069456
PCT Pub. Date: Apr. 3, 2025

(65) Prior Publication Data

US 2026/0145010 A1 May 28, 2026

(30) Foreign Application Priority Data

Sep. 28, 2023 (JP) ................................ 2023-167661

(51) Int. Cl.
*A61N 7/02* (2006.01)
*A61B 8/00* (2006.01)
(Continued)

(52) U.S. Cl.
CPC ................ *A61N 7/02* (2013.01); *A61B 8/085* (2013.01); *A61B 8/463* (2013.01); *A61B 8/486* (2013.01);
(Continued)

(58) Field of Classification Search
CPC .............. A61N 7/02; A61N 2007/0039; A61N 2007/0082; A61B 8/085; A61B 8/463;
(Continued)

(56) References Cited

U.S. PATENT DOCUMENTS

| | | | |
|---|---|---|---|
| 2007/0055155 | A1 | 3/2007 | Owen et al. |
| 2008/0228076 | A1 | 9/2008 | Azuma et al. |

(Continued)

FOREIGN PATENT DOCUMENTS

| | | | |
|---|---|---|---|
| CN | 109431536 | A | 3/2019 |
| CN | 113438927 | A | 9/2021 |

(Continued)

OTHER PUBLICATIONS

Yoshida et al.; "Highly sensitive ultrasound bubble imaging by triplet pulse sequence with interleaved HIFU pulses between imaging pulses"; provided by client on Apr. 16, 2025; 2 pages total.

(Continued)

*Primary Examiner* — Mark D Remaly
(74) *Attorney, Agent, or Firm* — Christensen O'Connor Johnson Kindness PLLC

(57) ABSTRACT

The present invention is aimed toward facilitating confirmation that an affected area has been sonicated with therapeutic ultrasonic waves in a treatment performed using an ultrasonic therapeutic apparatus. During therapeutic ultrasound transmitting processing, an ultrasonic transducer is caused to transmit the therapeutic ultrasonic wave. During sonicated-region image generating processing, after the therapeutic ultrasonic wave is transmitted, the ultrasonic probe is caused to transmit a plurality of imaging pulses or a plurality of ultrasonic waves at different time points and with different phases, and a plurality of received signals based on a plurality of reflected ultrasonic waves that have been reflected by body tissue and received by the ultrasonic
(Continued)

probe are summed, to thereby generate sonicated-region data based on nonlinear components of the respective received signals. During auxiliary ultrasound transmitting processing, the ultrasonic transducer is caused to transmit an interleaved pulse.

9 Claims, 8 Drawing Sheets

(51) Int. Cl.
*A61B 8/08* (2006.01)
*A61N 7/00* (2006.01)

(52) U.S. Cl.
CPC .......... *A61B 8/5207* (2013.01); *A61B 8/5246* (2013.01); *A61B 8/54* (2013.01); *A61N 2007/0039* (2013.01); *A61N 2007/0082* (2013.01)

(58) Field of Classification Search
CPC ..... A61B 8/486; A61B 8/5207; A61B 8/5246; A61B 8/54
See application file for complete search history.

(56) References Cited

U.S. PATENT DOCUMENTS

| | | | |
|---|---|---|---|
| 2010/0280373 | A1 | 11/2010 | Fan et al. |
| 2012/0157842 | A1 | 6/2012 | Davis et al. |
| 2013/0296743 | A1 | 11/2013 | Lee et al. |
| 2019/0269385 | A1 | 9/2019 | Ebbini et al. |
| 2020/0254285 | A1 | 8/2020 | Jang et al. |
| 2021/0212709 | A1 | 7/2021 | Cardiawave et al. |
| 2024/0225593 | A1 | 7/2024 | Umemura et al. |
| 2025/0018229 | A1 | 1/2025 | Nemoto et al. |

FOREIGN PATENT DOCUMENTS

| | | | |
|---|---|---|---|
| JP | 8-71069 | A | 3/1996 |
| JP | 20180050758 | A | 4/2018 |
| JP | 20210523776 | A | 9/2021 |
| JP | 2023079320 | A | 6/2023 |
| JP | 20230099937 | A | 7/2023 |
| WO | 2005/087109 | A1 | 9/2005 |
| WO | 20170126037 | A1 | 7/2017 |

OTHER PUBLICATIONS

Decision of Refusal (with English Translation) received for Japanese Application No. 2023-167661 dated Feb. 28, 2025; 14 pages total.

Notice of Reasons for Refusal (with English translation) received for JP Application No. 2023-167661 dated Oct. 25, 2024; 12 pages total.

International Search Report & Written Opinion (with English translation) dated Feb. 1, 2024 and received for JP Application No. PCT/JP2023/044507, filed Dec. 12, 2023; 15 pages total.

Extended European Search Report mailed Dec. 22, 2025, issued in corresponding European Application No. 23953278.1, filed Dec. 12, 2023, 20 pages.

Kannoto et al; "Effect of focal shift in the direction of propagation on time variation of bubble regions in bubble-enhanced ultrasonic heating"; dated Nov. 30, 2022; 4 pages total (partial English translation provided).

Office Action mailed Sep. 24, 2025, issued in corresponding Taiwanese Patent Application No. 113102230, filed Jan. 19, 2024, 14 pages.

Taiwanese Office Action (with partial English translation) issued on Feb. 10, 2026, received for corresponding Taiwanese Application No. 113102230.

ULTRASONIC THERAPEUTIC APPARATUS

CROSS-REFERENCE TO RELATED APPLICATIONS

This application is a U.S. National Stage Application of PCT/JP2023/044507, filed Dec. 12, 2023, which claims the benefit of JP 2023-167661, filed Sep. 28, 2023, the disclosures of which are incorporated herein in their entirety.

TECHNICAL FIELD

The present invention relates to an ultrasonic therapeutic apparatus, and more particularly to an apparatus including an ultrasonic transducer for treatment and an ultrasonic probe for image generation.

BACKGROUND

Therapeutic apparatuses in which high-intensity focused ultrasound therapy is adopted are widely used. Such a therapeutic apparatus is referred to as a high-intensity focused ultrasound (HIFU) sonication apparatus or a HIFU sonication system, which sonicates a site to be treated or a treatment target with ultrasonic waves to destroy tissue.

A HIFU sonication apparatus typically includes a plurality of ultrasonic transducers disposed on a semi-sphere or bowl face. The plurality of ultrasonic transducers are disposed to allow ultrasonic waves emanating from the respective ultrasonic transducers to be focused on a single point to form a focal point. During treatment, the focal point is aligned with a treatment target, which is then sonicated with ultrasonic waves. The sonicated location is confirmed using an ultrasonic imaging device that indicates the focal point on an ultrasonic image.

Patent Document 1 listed below discloses an ultrasonic therapeutic apparatus that observes the location of a focal point using an ultrasonic imaging device that displays a B-mode image (tomographic image). This apparatus emits from therapeutic ultrasonic transducers ultrasonic waves of weak level that do not affect tissue, and transmits and receives ultrasonic waves with an ultrasonic imaging probe to display a tomographic image. Acoustic properties of tissue of a test subject change with the temperature of the tissue; therefore, the tomographic image indicates the location of a focal point with different levels of brightness.

Patent Document 2 discloses, as a technology related to the invention of the present application, a technology for distinguishing echo components generated in a microbubble contrast medium by scattering, from components produced by nonlinear propagation of transmitted pulses.

CITATION LIST

Patent Literature

[Patent Document 1] JP H8-71069 A
[Patent Document 2] WO 2005/087109
[Patent Document 3] JP 2023-79320 A

SUMMARY

Technical Problem

Typically, an affected area of body tissue, upon being sonicated with a high-intensity therapeutic ultrasonic wave, generates bubbles (cavities) due to cavitation at a sonicated site. In a treatment using a conventional HIFU sonication apparatus, sonication of an affected area with therapeutic ultrasonic waves is confirmed by observation of the location of bubbles formed by cavitation and observation of body tissue of a patient. The location of bubbles is observed using harmonic imaging by transmitting ultrasonic waves from an ultrasonic probe toward the affected area and receiving harmonic waves generated from around the bubbles with the ultrasonic probe, as disclosed in Patent Document 3, for example. The body tissue of the patient is observed based on a B-mode image acquired by transmission and reception of ultrasonic waves with the ultrasonic probe.

In a treatment using a HIFU sonication apparatus for a narrow affected area, for example, therapeutic ultrasonic waves are transmitted within a small area, resulting in generation of only a small amount of bubbles. This may make confirmation of the affected area sonicated with therapeutic ultrasonic waves difficult.

The present invention is aimed toward facilitating confirmation that an affected area has been sonicated with therapeutic ultrasonic waves in a treatment performed with an ultrasonic therapeutic apparatus.

Solution to Problem

The present invention includes an ultrasonic transducer for treatment, an ultrasonic probe, and a control unit configured to control the ultrasonic transducer and the ultrasonic probe. The control unit is configured to execute therapeutic ultrasound transmitting processing for causing the ultrasonic transducer to transmit a therapeutic ultrasonic wave; auxiliary ultrasound transmitting processing for causing the ultrasonic transducer to transmit an auxiliary ultrasonic wave; and sonicated-region image generating processing for causing the ultrasonic probe to transmit a plurality of ultrasonic waves at different time points and with different phases after the therapeutic ultrasonic wave is transmitted, and combining a plurality of received signals based on a plurality of reflected ultrasonic waves that have been reflected by body tissue and received by the ultrasonic probe, to thereby generate sonicated-region data based on nonlinear components based on the respective received signals. The auxiliary ultrasound transmitting processing includes processing for causing the ultrasonic transducer to transmit the auxiliary ultrasonic wave at a time point between two time points at which two of the plurality of ultrasonic waves that are adjacent to each other on a time axis are transmitted.

Preferably, the auxiliary ultrasound transmitting processing includes processing for causing the ultrasonic transducer to transmit the auxiliary ultrasonic wave at a time point that is earlier than an intermediate time point between two time points at which two of the plurality of ultrasonic waves that are adjacent to each other on a time axis are transmitted.

Preferably, the auxiliary ultrasound transmitting processing includes processing for causing the ultrasonic transducer to transmit the auxiliary ultrasonic wave, after the therapeutic ultrasonic wave is transmitted, at a time point that is earlier than time points at which the plurality of ultrasonic waves are transmitted.

Preferably, the plurality of ultrasonic waves comprise M ultrasonic waves, and the plurality of received signals are signals based on the plurality of reflected ultrasonic waves received by the ultrasonic probe, based on the M ultrasonic waves sequentially transmitted from the ultrasonic probe with a phase difference of 360°/M.

Preferably, the control unit is configured to execute B-mode image generating processing for generating B-mode image data of the body tissue by using one of the plurality of received signals.

Preferably, the control unit is configured to cause the display device to display a sonicated-region image based on the sonicated-region data and a B-mode image based on the B-mode image data.

Preferably, the control unit is configured to cause the display device to display in a superimposed manner the sonicated-region image based on the sonicated-region data and the B-mode image based on the B-mode image data.

Advantageous Effects of Invention

The present invention facilitates confirmation that an affected area has been sonicated with therapeutic ultrasonic waves.

DESCRIPTION OF EMBODIMENTS

Figure 1:
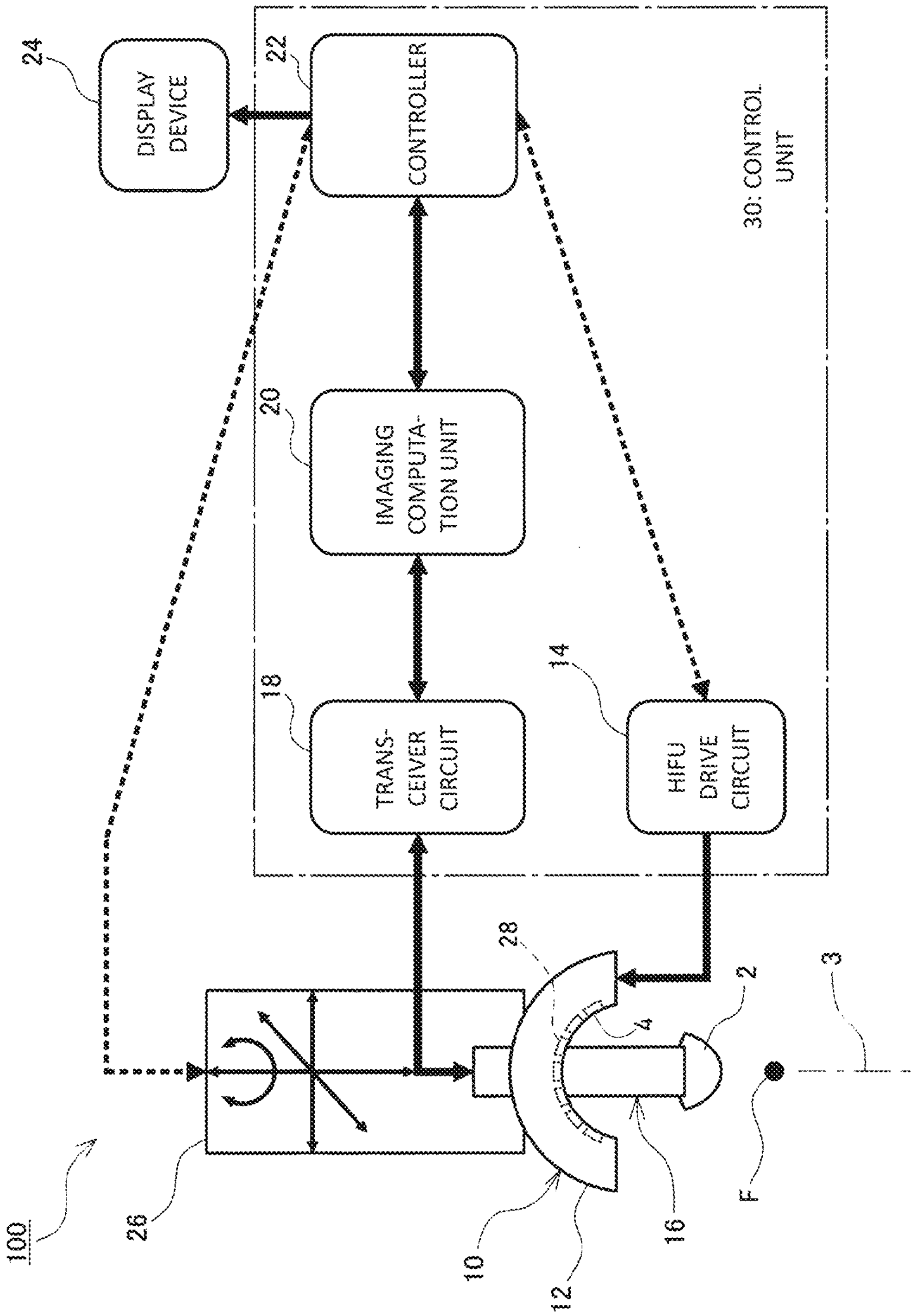
FIG. 1 illustrates a configuration of a HIFU sonication apparatus.

An embodiment of the present invention will be described by reference to the drawings. In the drawings, identical elements are denoted with identical reference numerals and their descriptions are not repeated. FIG. 1 illustrates a configuration of a HIFU sonication apparatus 100 (ultrasonic therapeutic apparatus) according to an embodiment of the present invention. The HIFU sonication apparatus 100 includes a HIFU transducer unit 10, a HIFU drive circuit 14, an ultrasonic probe 16, a transceiver circuit 18, an imaging computation unit 20, a controller 22, a display device 24, and a drive device 26.

The controller 22 may be a personal computer or a tablet computer, for example. An operation device (not shown) that allows a user to operate the HIFU sonication apparatus 100 is connected to the controller 22. The operation device may include a mouse, a touch panel integrated with the display device 24, a switch, and a keyboard, for example.

The HIFU transducer unit 10 includes a transducer housing 12 having a concavity 4 opened downward, and a plurality of ultrasonic transducers 28 arranged along the concavity 4 of the transducer housing 12 and secured to the transducer housing 12. It may be the case that the HIFU transducer unit 10 has substantial HIFU concavity 4. In this configuration, the ultrasonic transducers 28 may be secured to the transducer housing 12 in a manner that the ultrasonic transducers 28 are arranged along a virtual concavity 4.

The concavity 4 of the transducer housing 12 may have a shape similar to a shape of a side face of a cone. The cone as used herein refers to a three-dimensional shape formed of a set of straight lines extending from one point within a space to a bottom face, The concavity 4 of the transducer housing 12 may also have a shape expanding upward in a dome shape. The ultrasonic transducers 28 are secured to the transducer housing 12 in such a manner that ultrasonic waves emitted from the respective ultrasonic transducers 28 have an increased intensity at a focal point F beneath the transducer housing 12.

The HIFU drive circuit 14 causes each ultrasonic transducer 28 of the HIFU transducer unit 10 to generate ultrasonic waves under control of the controller 22. The HIFU drive circuit 14 further adjusts the intensity of the ultrasonic waves emitted from each ultrasonic transducer 28 under control of the controller 22.

The ultrasonic probe 16 is secured to the transducer housing 12 to transmit and receive the ultrasonic waves at a location beneath the transducer housing 12 and above the focal point F. In this embodiment, the ultrasonic probe 16 extends vertically through the top of the transducer housing 12, with a transceiver unit 2 that transmits and receives the ultrasonic waves, facing downward.

The transceiver circuit 18 and the imaging computation unit 20 may be those of a typical ultrasonic imaging device. The imaging computation unit 20 may be composed of a processor that executes a program to control the transceiver circuit 18. The transceiver circuit 18 executes the following processing under control of the imaging computation unit 20. Specifically, the transceiver circuit 18 causes the ultrasonic probe 16 to transmit an ultrasonic wave to scan a beam based on the transmitted ultrasonic wave (ultrasound beam). The ultrasound beam is scanned with an observation face including a center axis 3 extending vertically from the top of the transducer housing 12. The transceiver circuit 18 further causes the ultrasonic probe 16 to receive reflected ultrasonic waves from a direction in which the ultrasound beam is directed, and acquires, from the ultrasonic probe 16, received signals based on the reflected ultrasonic waves received from each direction in which the ultrasound beam is directed. The transceiver circuit 18 outputs each received signal to the imaging computation unit 20.

The imaging computation unit 20 generates ultrasound data based on each received signal output from the transceiver circuit 18. The ultrasound data may be sonicated-region data representing a region of body tissue of a patient where nonlinear components are generated, or B-mode image data representing a B-mode image (tomographic image) acquired with regard to body tissue of a patient.

The drive device 26 moves the HIFU transducer unit 10 and the ultrasonic probe 16 under control of the controller 22 to adjust the positions of the HIFU transducer unit 10 and the ultrasonic probe 16, respectively. The drive device 26, under control of the controller 22, may rotate the ultrasonic probe 16 about the center axis 3 to rotate the observation face of the ultrasonic probe 16 about the center axis 3.

Prior to sonicating the patient with therapeutic ultrasonic waves from the HIFU transducer unit 10, positioning as described below is executed. The HIFU drive circuit 14 causes each of the ultrasonic transducers 28 to transmit ultrasonic waves of an intensity that is lower than the intensity of the ultrasonic waves to be applied during treatment. The drive device 26 sets the rotation angle position of the ultrasonic probe 16 to allow the ultrasonic probe 16 to scan the ultrasound beam with the observation face at a predetermined rotation angle position.

The imaging computation unit 20 causes the ultrasonic probe 16 to scan the ultrasound beam with the observation face, acquires the B-mode image data or the ultrasound data, and outputs the B-mode image data to the controller 22. The controller 22 causes the display device 24 to display the B-mode image. The user or practitioner references the B-mode image displayed on the display device 24 to confirm a difference between the location where the intensity of the ultrasonic wave transmitted from the HIFU transducer unit 10 is increased (focal point) and the location of the affected area.

When the difference between the location of the focal point and the location of the affected area is not within the allowable range, the user changes the locations or positions of the ultrasonic probe 16 and the HIFU transducer unit 10. After confirming that the location of the focal point F and the location of the affected area match or that the difference between the location of the focal point F and the location of the affected area falls within the allowable range, the user operates the controller 22 for treatment. The controller 22 controls the HIFU drive circuit 14 in accordance with the user operation. The HIFU drive circuit 14 causes each ultrasonic transducer 28 to transmit a therapeutic ultrasonic wave having an intensity required for the treatment under control of the controller 22. This achieves cauterization of the body tissue at the focal point F for treatment.

The HIFU sonication apparatus 100 executes, while sonicating the patient with therapeutic ultrasonic waves, sonicated-region display processing for displaying on the display device 24 an image representing a sonicated region that is sonicated with the therapeutic ultrasonic waves (sonicated-region image). The sonicated-region image and the B-mode image may be displayed side by side, or the sonicated-region image may be displayed in a superimposed manner on the B-mode image. Here, the processing for displaying the two images in a superimposed manner may be processing for generating new image data by combining the image data to enable one image to be seen through the other image, and displaying an image based on the new image data.

Figure 2:
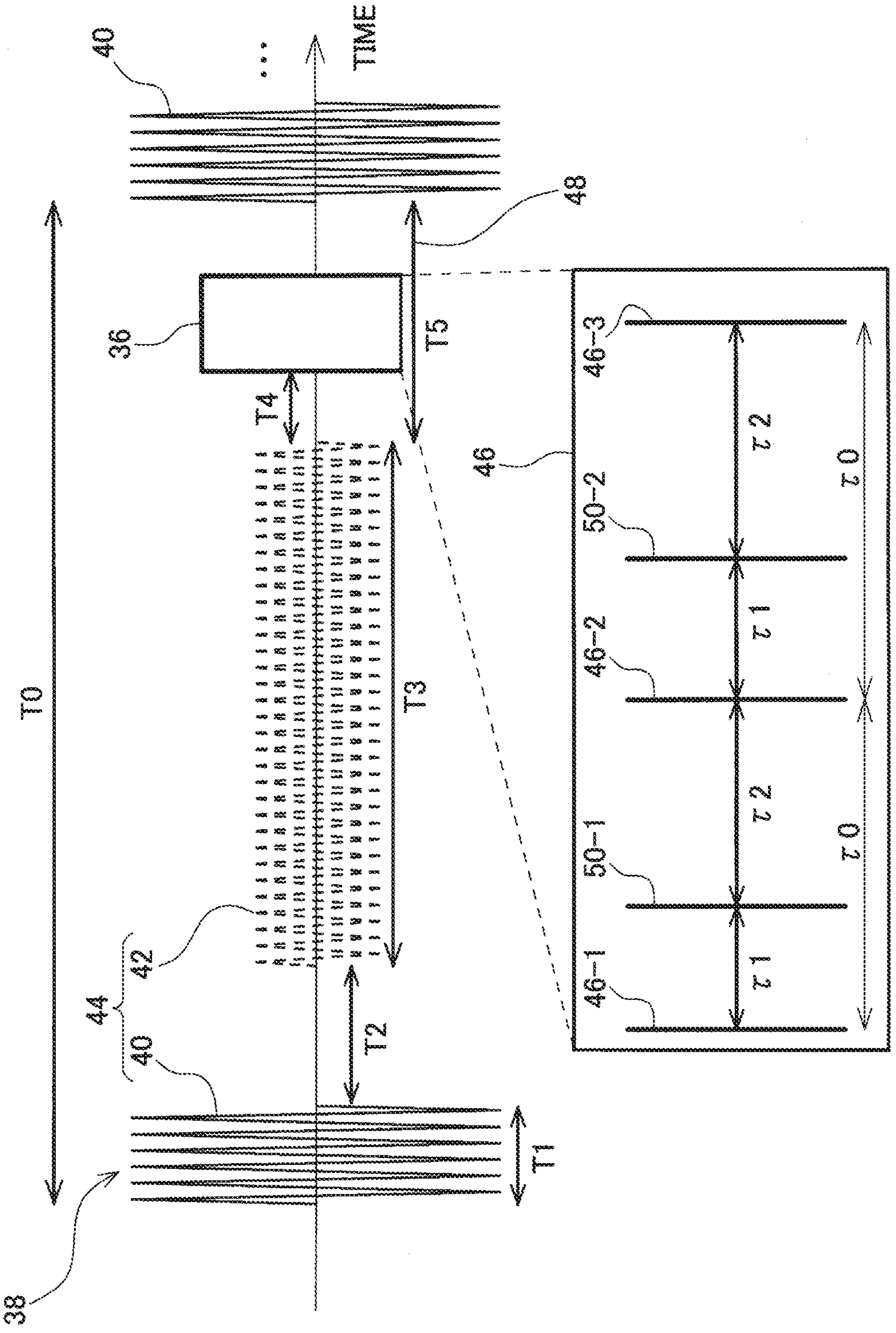
FIG. 2 conceptually shows transmission timing of therapeutic ultrasonic waves and HIFU/imaging mixture waves.

FIG. 2 conceptually shows transmission timing of a therapeutic ultrasonic wave 38 transmitted from the HIFU transducer unit 10 and a HIFU/imaging mixture wave 36 transmitted from the HIFU transducer unit 10 and the ultrasonic probe 16 during execution of the sonicated-region display processing.

The therapeutic ultrasonic wave 38 comprises a therapeutic ultrasonic pulse 44 including a trigger pulse 40, and a heating burst 42 following the trigger pulse 40. The therapeutic ultrasonic pulse 44 is transmitted repeatedly from the HIFU transducer unit 10 over time. An sonication pause period 48 is provided between two therapeutic ultrasonic pulses 44 adjacent to each other on a time axis, and transmission of the therapeutic ultrasonic wave 38 is interrupted during the sonication pause period 48. The amplitude of heating burst 42 may be smaller than the amplitude of the trigger pulse 40. The trigger pulse 40 has a time length T1 that may be shorter than a time length T3 of the heating burst 42.

Transmission of the therapeutic ultrasonic pulse 44 from the HIFU transducer unit 10 causes cauterization of body tissue at the focal point F. The body tissue, when sonicated with the trigger pulse 40, generates bubbles, and the state in which bubbles are generated is maintained by sonication with the heating burst 42.

During the sonication pause period 48, the HIFU/imaging mixture wave 36 is transmitted from the HIFU transducer unit 10 and the ultrasonic probe 16. The HIFU/imaging mixture wave 36 includes a first imaging pulse 46-1, a second imaging pulse 46-2, and a third imaging pulse 46-3 transmitted from the ultrasonic probe 16 at time intervals of time τ0. The second imaging pulse 46-2 is delayed by a phase of 120° with respect to the first imaging pulse 46-1, and the third imaging pulse 46-3 is delayed by a phase of 120° with respect to the second imaging pulse 46-2. In the following description, any one of the first imaging pulse 46-1, the second imaging pulse 46-2, and the third imaging pulse 46-3, which is not specified, may be referred to simply as an imaging pulse 46.

The HIFU/imaging mixture wave 36 further includes a first interleaved pulse 50-1 and a second interleaved pulse 50-2 transmitted from the HIFU transducer unit 10. In the following description, either one of the first interleaved pulse 50-1 and the interleaved pulse 50-2, which is not specified, may be referred to simply as an interleaved pulse 50.

The first interleaved pulse 50-1 is transmitted at a time point between two time points at which the first imaging pulse 46-1 and the second imaging pulse 46-2 are respectively transmitted, and the second interleaved pulse 50-2 is transmitted at a time point between two time points at which the second imaging pulse 46-2 and the third imaging pulse 46-3 are respectively transmitted.

Specifically, upon elapse of a time period τ1 after transmission of the first imaging pulse 46-1, the first interleaved pulse 50-1 is transmitted, and upon elapse of a time period τ2 after transmission of the first interleaved pulse 50-1, the second interleaved pulse 50-2 is transmitted. Further, upon elapse of the time period τ1 after transmission of the second imaging pulse 46-2, the second interleaved pulse 50-2 is transmitted, and upon elapse of the time period τ2 after transmission of the second interleaved pulse 50-2, the third interleaved pulse 50-3 is transmitted.

The time period τ1 is shorter than the time period τ2. Thus, the first interleaved pulse 50-1 is transmitted at a time point that is earlier than an intermediate time point between the time point at which the first imaging pulse 46-1 is transmitted and the time point at which the second imaging pulse 46-2 is transmitted. The intermediate time point as used herein refers to a time point corresponding to a midpoint between two points on the time axis. Further, the second interleaved pulse 50-2 is transmitted at a time point that is earlier than an intermediate time point between the time point at which the second imaging pulse 46-2 is transmitted and the time point at which the third imaging pulse 46-3 is transmitted.

The time period τ1 and the time period τ2 may be determined to allow the HIFU/imaging mixture wave 36 to work in the body tissue as follows. The first interleaved pulse 50-1 reaches the affected area after the reflected ultrasonic wave generated based on the first imaging pulse 46-1 is received by the ultrasonic probe 16, and causes bubbles generated in the affected area to oscillate. The second imaging pulse 46-2 reaches the affected area after multiple reflected pulses generated in the body tissue by the first interleaved pulse 50-1 are sufficiently attenuated. The second interleaved pulse 50-2 reaches the affected area after the reflected ultrasonic wave generated based on the second imaging pulse 46-2 is received by the ultrasonic probe 16, and causes bubbles generated in the affected area to oscillate. The third imaging pulse 46-3 reaches the affected area after multiple reflected pulses generated in the body tissue by the second interleaved pulse 50-2 are sufficiently attenuated.

Figure 3:
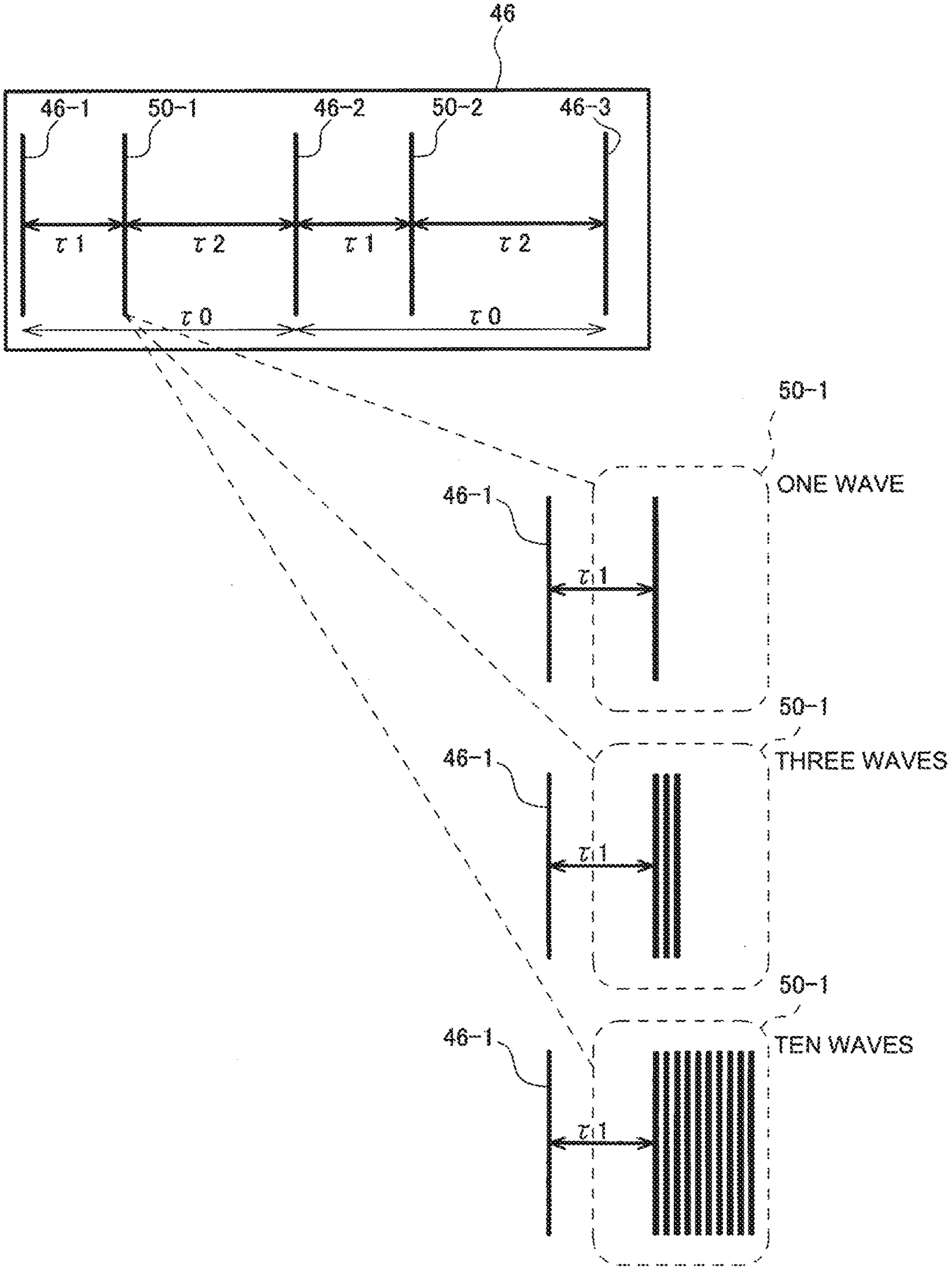
FIG. 3 illustrates configurations of an interleaved pulse.

Each interleaved pulse 50 may be composed of a single ultrasonic pulse or of a plurality of ultrasonic pulses that are arranged in a line on the time axis. FIG. 3 shows, in a lower right part, from top to bottom, the timing of the interleaved pulse 50 composed of a single ultrasonic pulse, the interleaved pulse 50 composed of three ultrasonic pulses, and the interleaved pulse 50 composed of ten ultrasonic pulses, respectively.

While in the example illustrated in FIG. 2, the time period from transmission of the first imaging pulse 46-1 to transmission of the first interleaved pulse 50-1 is equal to the time period from transmission of the second imaging pulse 46-2 to transmission of the second interleaved pulse 50-2, these time periods may be different from each other.

Each imaging pulse 46 is reflected within the body tissue. Reflection of the imaging pulses 46 around bubbles generated due to the therapeutic ultrasonic pulses 44 causes generation of nonlinear components such as harmonic waves. The reflected ultrasonic waves reflected from the body tissue therefore contain, in addition to fundamental waves, the nonlinear components originated from the bubbles. Typically, the greater the amount of bubbles that are generated, the higher the intensity of the nonlinear components that are generated.

Returning again to FIG. 1, processing performed by the HIFU sonication apparatus 100 for receiving reflected ultrasonic waves for the respective imaging pulses 46 will be described. The ultrasonic probe 16 receives a first reflected ultrasonic wave, a second reflected ultrasonic wave, and a third reflected ultrasonic wave for the first imaging pulse 46-1, the second imaging pulse 46-2, and the third imaging pulse 46-3, respectively, and outputs a first received signal, a second received signal, and a third received signal, respectively, to the transceiver circuit 18. The transceiver circuit 18 performs amplification, for example, on the first to third received signals, and outputs the amplified received signals to the imaging computation unit 20.

The imaging computation unit 20 sums up the first received signal, the second received signal, and the third received signal, to generate a nonlinear signal containing a sum of nonlinear components contained in the first to third received signals. In the signal obtained by summing the first to third received signals, the fundamental wave components are reduced due to the phase relation of the first imaging pulse 46-1, the second imaging pulse 46-2, and the third imaging pulse 46-3. The imaging computation unit 20 generates the nonlinear signals with respect to the first to third reflected ultrasonic waves coming from the respective directions to which the ultrasonic beam is directed, and generates sonicated-region data based on the nonlinear signals generated for the respective directions. The sonicated-region data are image data representing a sonicated-region image indicating a region where the bubbles are generated, in a region in which the ultrasound beams are scanned.

The imaging computation unit 20 further generates a B-mode image based on one of the first reflected ultrasonic wave to the third reflected ultrasonic wave. For example, the imaging computation unit 20 generates, based on the second reflected ultrasonic wave coming from each direction to which the ultrasonic beam is directed, pixel data of the B-mode image for each direction, and generates B-mode image data based on the pixel data acquired for each direction. The source reflected ultrasonic wave for generating the B-mode image data may be the first reflected ultrasonic wave or the third reflected ultrasonic wave.

The imaging computation unit 20 outputs the sonicated-region data and the B-mode image data to the controller 22. The controller 22, based on the sonicated-region data and the B-mode image data, causes the display device 24 to display an image including the sonicated region image superimposed on the B-mode image (B-mode sonicated-region image).

The imaging computation unit 20 outputs the sonicated-region data and the B-mode image data at a frame time interval (the inverse of a frame rate) to the controller 22. The controller 22 causes the display device 24 to sequentially display the B-mode sonicated-region images over time.

The controller 22 may display the sonicated region image and the B-mode image individually, rather than in a superimposed manner. For example, the controller 22 may cause the display device 24 to display the sonicated-region image and the B-mode image such that these images are arranged in a comparable manner.

Figure 4:
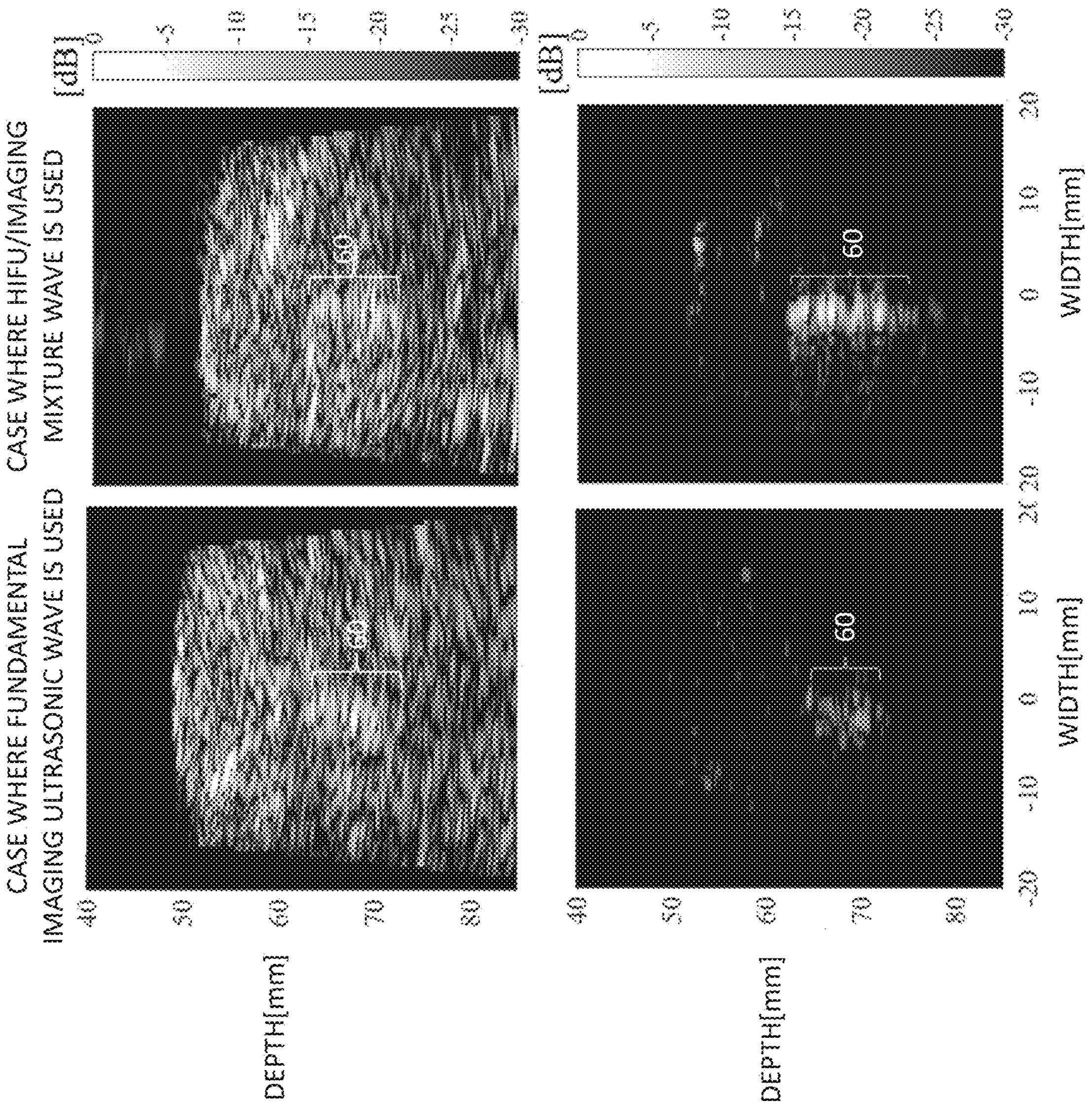
FIG. 4 shows an experimental result of a B-mode image and a sonicated-region image.

FIG. 4 shows an experimental result. The upper left part and the lower left part of FIG. 4 show, respectively, a B-mode image and a sonicated-region image that are generated using conventional fundamental imaging ultrasonic waves. The fundamental imaging ultrasonic wave corresponds to the HIFU/imaging mixture wave 36 without the first interleaved pulse 50-1 and the second interleaved pulse 50-2. In transmission of the fundamental imaging ultrasonic wave, after elapse of the time period τ0 from transmission of the first imaging pulse 46-1, with no first interleaved pulse 50-1 being transmitted, the second imaging pulse 46-2 is transmitted. Further, after elapse of the time period to from transmission of the second imaging pulse 46-2, with no second interleaved pulse 50-2 being transmitted, the third imaging pulse 46-3 is transmitted. In each figure, the horizontal axis indicates a width [mm] and the vertical axis indicates a depth [mm]. An image of bubbles 60 is included in each figure.

The upper right part and the lower right part of FIG. 4 show, respectively, a B-mode image and a sonicated-region image according to the present embodiment generated using the HIFU/imaging mixture wave 36. The interleaved pulse 50 that was used is composed of three ultrasonic pulses sequentially arranged on the time axis. In each figure, the horizontal axis indicates a width [mm] and the vertical axis indicates a depth [mm]. An image of the bubbles 60 is included in each figure. As is clear from the lower left figure and the lower right figure, the image generated using the HIFU/imaging mixture waves 36 shows the bubbles 60 generated in the sonicated region more clearly than the image generated using the fundamental imaging ultrasonic wave.

Figure 5:
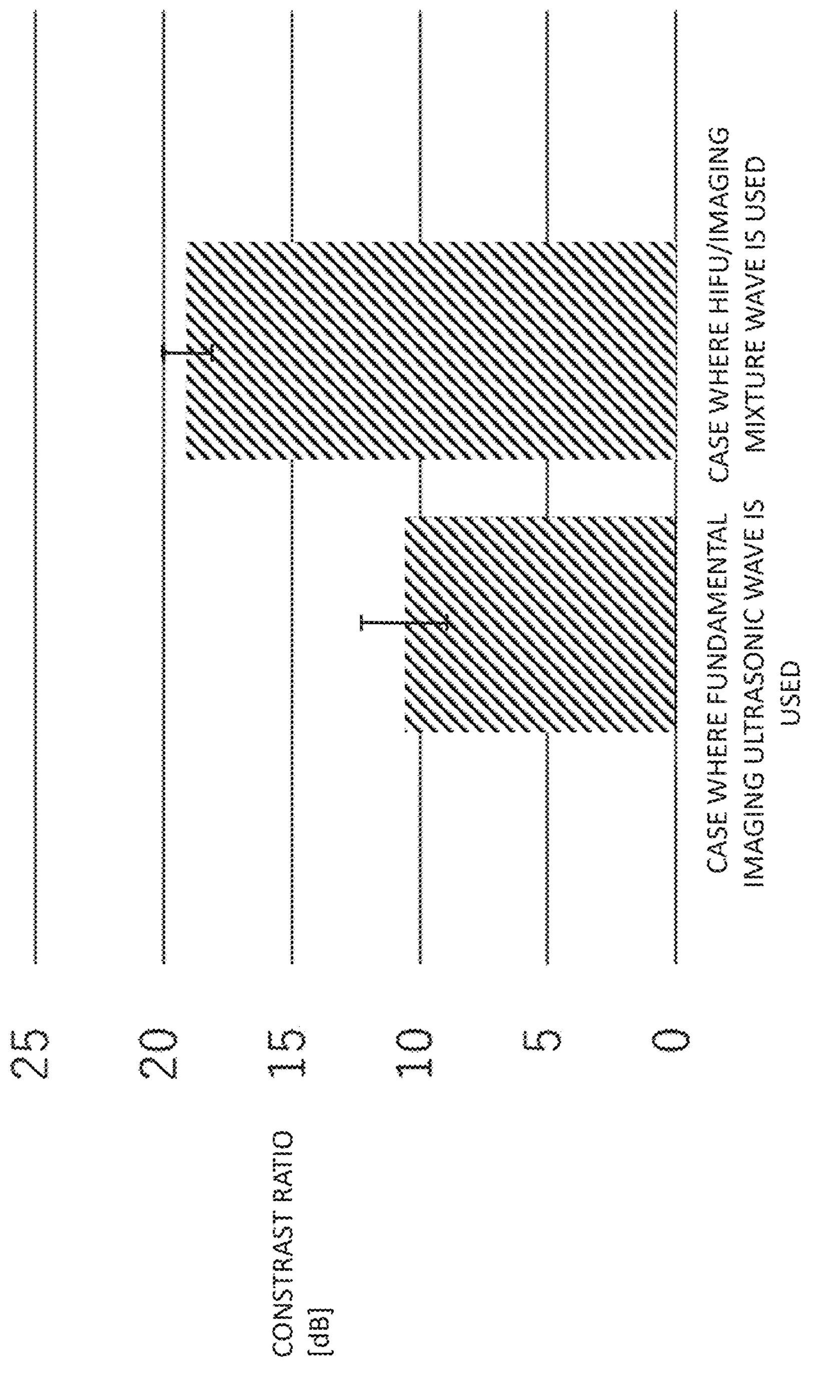
FIG. 5 shows an experimental result of contrast ratios of a sonicated-region image.

FIG. 5 shows bubble-to-tissue contrast ratios (hereinafter referred to as "contrast ratio") of the sonicated-region image. The contrast ratio of the image generated using the HIFU/imaging mixture waves 36 is higher than the contrast ratio of the image generated using the fundamental imaging ultrasonic wave with no interleaved pulse 50, by about 9 dB. The conditions of the experiment are as follows. The period T0 from transmission of a certain trigger pulse 40 to transmission of the subsequent trigger pulse 40 is 50 msec. The time length T1 of the trigger pulse 40 is 0.1 msec. The time period T2 from completion of transmission of the trigger pulse 40 to start of transmission of the heating burst 42 is 3 msec. The time length T3 of the heating burst 42 is 43.9 ms. The time period T4 from completion of transmission of the heating burst 42 to start of transmission of the HIFU/imaging mixture wave 36 is 1 ms. The time period τ1 in the HIFU/imaging mixture wave 36 is 120 μsec, and the time period τ2 is 280 μsec. The sonication pause period T5 is 3 msec.

Figure 6:
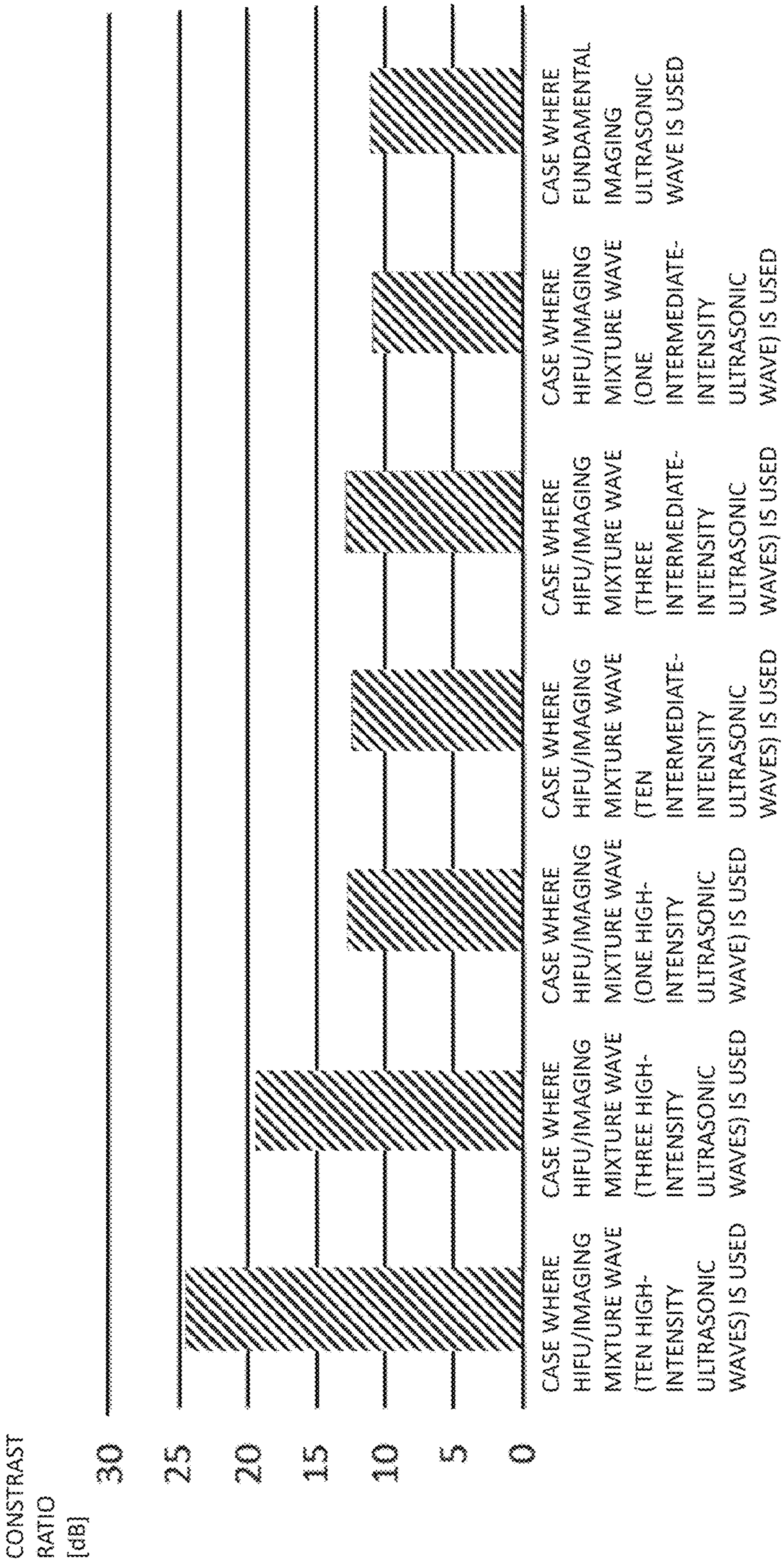
FIG. 6 shows an experimental result of the contrast ratios of a sonicated-region image.

FIG. 6 shows the contrast ratios of the sonicated-region images using the HIFU/imaging mixture waves 36 having different configurations. The first to third figures from the left sequentially show the contrast ratio for an example including the interleaved pulse 50 composed of ten high-intensity ultrasonic pulse waves, the contrast ratio for an example including the interleaved pulse 50 composed of three high-intensity ultrasonic pulse waves, and the contrast ratio for an example including the interleaved pulse 50 composed of one high-intensity ultrasonic pulse wave, respectively. The fourth to sixth figures from the left sequentially show the contrast ratio for an example including the interleaved pulse 50 composed of ten intermediate-intensity ultrasonic pulse waves, the contrast ratio for an example including the interleaved pulse 50 composed of three intermediate-intensity ultrasonic pulse waves, and the contrast ratio for an example including the interleaved pulse 50 composed of one intermediate-intensity ultrasonic pulse wave, respectively. The high-intensity ultrasonic pulse as used herein refers to an ultrasonic pulse with the same amplitude as that of the trigger pulse 40, and the intermediate-intensity ultrasonic pulse as used herein refers to an ultrasonic pulse with the same amplitude as that of the heating burst 42. The furthest right figure shows the contrast ratio for an example including the fundamental imaging ultrasonic wave.

As shown in FIG. 6, the contrast ratio tends to be higher with larger amplitude of the interleaved pulse 50 and with a greater number of the ultrasonic pulses forming the interleaved pulse 50.

As described above, the HIFU sonication apparatus 100 according to the present embodiment transmits the HIFU/imaging mixture waves 36 to thereby transmit the first interleaved pulse 50-1 between transmission of the first imaging pulse 46-1 and transmission of the second imaging pulse 46-2. The first interleaved pulse 50-1 transmitted to the affected area causes oscillation of bubbles generated in the affected area due to the therapeutic ultrasonic wave 38, to thereby increase the nonlinear components to be generated due to the second imaging pulse 46-2. Between the period from transmission of the second imaging pulse 46-2 and transmission of the third imaging pulse 46-3, the second interleaved pulse 50-2 is transmitted. The second interleaved pulse 50-2 transmitted to the affected area causes oscillation of the bubbles generated due to the therapeutic ultrasonic wave 38 in the affected area, to thereby increase the nonlinear components to be generated by the third imaging pulse 46-3. This increases the size of the nonlinear signals and emphasizes the bubbles appearing in the sonicated region image, which allows the user to easily confirm that the affected area has been sonicated with the therapeutic ultrasonic wave 38.

In the above example, the interleaved pulse 50 is transmitted at a time point between two time points at which two imaging pulses 46 adjacent to each other on the time axis are transmitted. However, the interleaved pulse 50 may be transmitted by the time point at which the imaging pulse 46 is transmitted for the first time after transmission of the therapeutic ultrasonic pulse 44.

Further, while in the above example, the imaging pulse 46 for generating the ultrasound data is transmitted three times, the imaging pulse 46 may be transmitted twice, or four or more times. When the imaging ultrasonic wave is transmitted M times (where M is an integer of 2 or greater), the phase difference between the imaging pulses 46 adjacent to each other on the time axis is 360°/M. Alternatively, the phase of each imaging ultrasonic wave may be set such that, irrespective of the order of transmission, the phase of $\theta+i\cdot 360°/M$ (where θ is an arbitrary phase, and i is an integer that is 0 to M−1) may be assigned to M imaging pulses 46.

The imaging computation unit 20 sums up the first received signal to the M-th received signal to generate a nonlinear signal containing the sum of nonlinear components contained in the first to M-th received signals. The imaging computation unit 20 further generates a B-mode image based on one of the first reflected ultrasonic wave to the M-th reflected ultrasonic wave.

While in the above embodiment, the therapeutic ultrasonic pulse 44 includes the trigger pulse 40 and the pulse containing the heating burst 42 following the trigger pulse 40, the therapeutic ultrasonic pulse 44 may include a pulse containing only the trigger pulse 40, with no heating burst 42 being contained.

Figure 7:
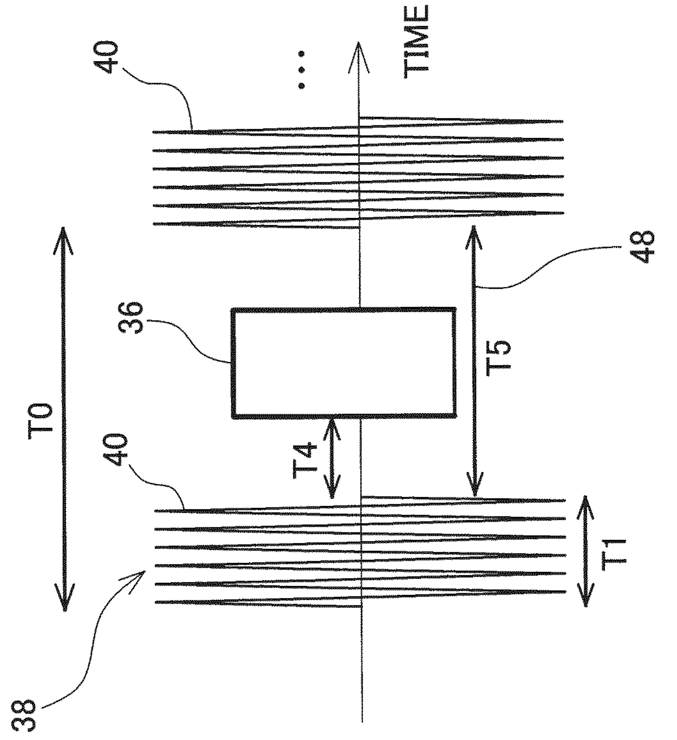
FIG. 7 conceptually shows transmission timing of therapeutic ultrasonic pulses including no heating burst and a HIFU/imaging mixture wave.

FIG. 7 conceptually shows transmission timing of the therapeutic ultrasonic pulse 44 that does not contain the heating burst 42, and the HIFU/imaging mixture wave 36. Upon elapse of the sonication pause period T5 after completion of transmission of a certain trigger pulse 40, the next trigger pulse 40 is transmitted. During the sonication pause period T5, the HIFU/imaging mixture wave 36 is transmitted upon elapse of the time period T4 after completion of transmission of the trigger pulse 40.

Figure 8:
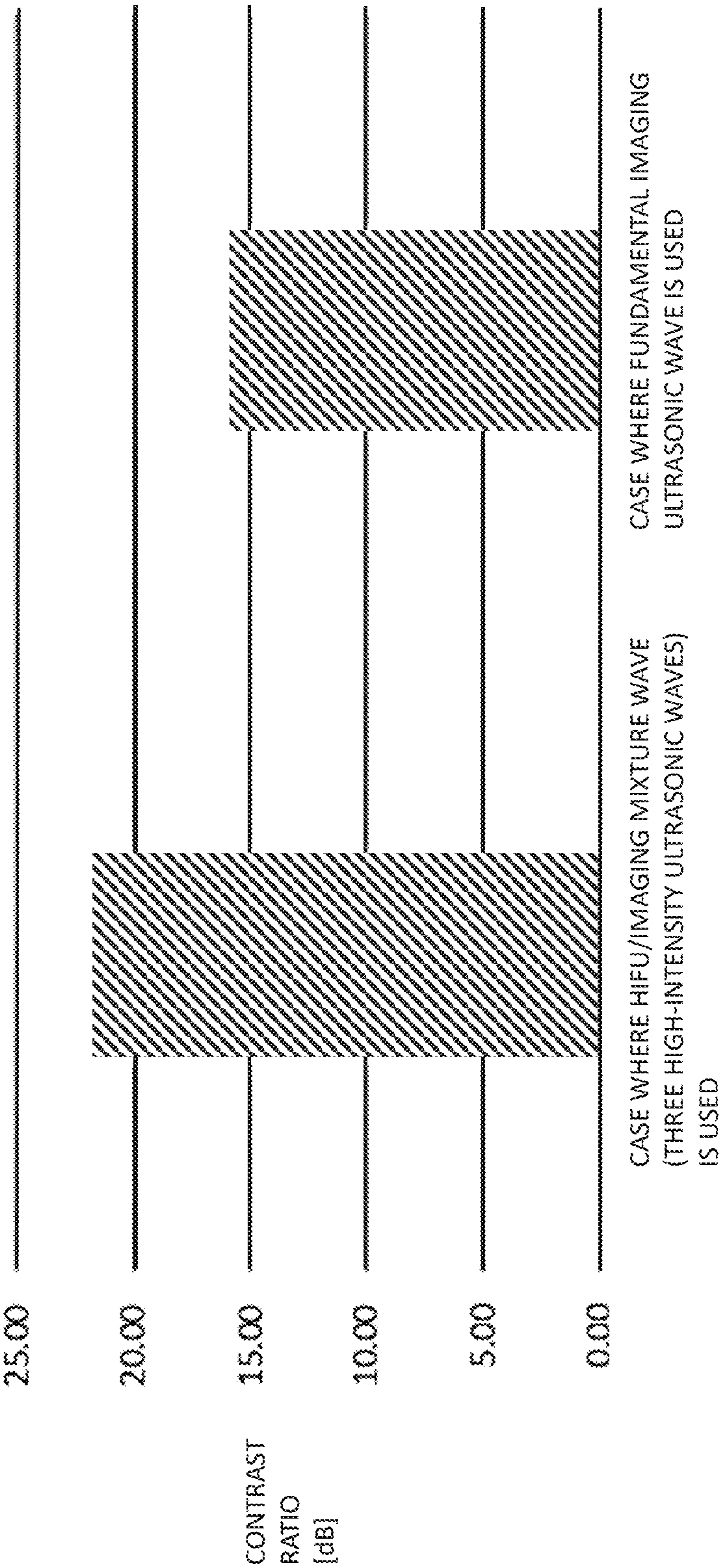
FIG. 8 shows an experimental result of the contrast ratios in an experiment with therapeutic ultrasonic pulses including no heating burst.

FIG. 8 shows the contrast ratios of images generated using the therapeutic ultrasonic pulse 44 with no heating burst 42. Specifically, the left part of FIG. 8 shows the contrast ratio regarding the HIFU/imaging mixture wave 36 containing the interleaved pulse 50 composed of three high-intensity ultrasonic pulses, and the right part of FIG. 8 shows the contrast ratio regarding the fundamental imaging ultrasonic wave. The contrast ratio of the image generated using the HIFU/imaging mixture wave 36 is higher than the contrast ratio of the image generated using the fundamental imaging ultrasonic wave by approximately 6 dB. Thus, the image generated using the HIFU/imaging mixture wave 36 tends to achieve a higher contrast ratio than the image generated using the fundamental imaging ultrasonic wave in the case where therapeutic ultrasonic pulse 44 contains no heating burst 42, similar to the case where the therapeutic ultrasonic pulse 44 contains the heating burst 42.

As described above, the HIFU sonication apparatus 100 includes the HIFU transducer unit 10 having the ultrasonic transducers 28 for treatment, the ultrasonic probe 16, and the control unit 30 that controls the ultrasonic transducers 28 and the ultrasonic probe 16. The control unit 30 is composed of the HIFU drive circuit 14, the transceiver circuit 18, the imaging computation unit 20, and the controller 22.

The control unit 30 executes therapeutic ultrasound transmitting processing, auxiliary ultrasound transmitting processing, and sonicated-region image generating processing. The therapeutic ultrasound transmitting processing is executed to cause the ultrasonic transducers 28 to transmit therapeutic ultrasonic wave 38. The sonicated-region image generating processing is executed after completion of transmission of the therapeutic ultrasonic wave 38. The sonicated-region image generating processing includes causing the ultrasonic probe 16 to transmit a plurality of imaging pulses 46 or a plurality of ultrasonic waves at different time points and summing (or combining) the first to M-th received signals (a plurality of received signals) based on the first to M-th reflected ultrasonic waves (a plurality of reflected ultrasonic waves) that have been reflected on body tissue and then received by the ultrasonic probe 16, thereby generating sonicated-region data based on nonlinear components of the respective received signals.

The auxiliary ultrasound transmitting processing includes processing of causing the ultrasonic transducers 28 to transmit the interleaved pulse 50 or auxiliary ultrasonic wave at a time point between two time points at which two imaging pulses 46 adjacent to each other on the time axis, of the plurality of imaging pulses 46, are transmitted.

The auxiliary ultrasound transmitting processing may include processing of causing the ultrasonic transducers 28 to transmit the interleaved pulse 50 or the auxiliary ultrasonic wave before transmission of the imaging pulses 46 after transmission of the therapeutic ultrasonic wave 38.

The control unit 30 executes B-mode image generating processing for generating B-mode mage data of body tissue with any one of the received signals.

The control unit 30 executes display processing to cause the display device 24 to display a sonicated-region image based on the sonicated-region data and a B-mode image based on the B-mode image data. The control unit 30 may cause the display device 24 to display the sonicated-region image and the B-mode image in a superimposed manner.

The above configuration and processing enable both sonication of the body tissue with the therapeutic ultrasonic wave 38 and display of a region sonicated with the therapeutic ultrasonic wave on the B-mode image. This enables the user to easily confirm that the affected area has been sonicated with the therapeutic ultrasonic waves 38. Further, transmission of the interleaved pulses 50 leads to an increase in the nonlinear components generated by the imaging pulses 46. This results in an increased size of nonlinear signals to emphasize the bubbles appearing in the sonicated-region image, thereby enabling the user to easily confirm that the affected area has been sonicated with the therapeutic ultrasonic waves 38.

CONFIGURATIONS OF PRESENT INVENTION

Configuration 1

An ultrasonic therapeutic apparatus comprising:

an ultrasonic transducer for treatment;

an ultrasonic probe; and a control unit configured to control the ultrasonic transducer and the ultrasonic probe, wherein the control unit is configured to execute:

therapeutic ultrasound transmitting processing for causing the ultrasonic transducer to transmit a therapeutic ultrasonic wave;

auxiliary ultrasound transmitting processing for causing the ultrasonic transducer to transmit an auxiliary ultrasonic wave; and sonicated-region image generating processing for causing the ultrasonic probe to transmit a plurality of ultrasonic waves at different time points and with different phases after the therapeutic ultrasonic wave is transmitted, and combining a plurality of received signals based on a plurality of reflected ultrasonic waves that have been reflected by body tissue and received by the ultrasonic probe, to thereby generate sonicated-region data based on nonlinear components based on the respective received signals, and wherein the auxiliary ultrasound transmitting processing includes processing for causing the ultrasonic transducer to transmit the auxiliary ultrasonic wave at a time point between two time points at which two of the plurality of ultrasonic waves that are adjacent to each other on a time axis are transmitted.

Configuration 2

The ultrasonic therapeutic apparatus according to Configuration 1, wherein the auxiliary ultrasound transmitting processing includes processing for causing the ultrasonic transducer to transmit the auxiliary ultrasonic wave at a time point that is earlier than an intermediate time point between two time points at which two of the plurality of ultrasonic waves that are adjacent to each other on a time axis are transmitted.

Configuration 3

The ultrasonic therapeutic apparatus according to Configuration 1 or 2, wherein the auxiliary ultrasound transmitting processing includes processing for causing the ultrasonic transducer to transmit the auxiliary ultrasonic wave, after the therapeutic ultrasonic wave is transmitted, at a time point that is earlier than time points at which the plurality of ultrasonic waves are transmitted.

Configuration 4

The ultrasonic therapeutic apparatus according to any one of Configurations 1 to 3, wherein the plurality of ultrasonic waves comprises M ultrasonic waves, and the plurality of received signals are signals based on the plurality of reflected ultrasonic waves received by the ultrasonic probe, based on the M ultrasonic waves sequentially transmitted from the ultrasonic probe with a phase difference of 360°/M.

Configuration 5

The control unit is the ultrasonic therapeutic apparatus according to Configurations 1 to 4, wherein the control unit is configured to execute B-mode image generating processing for generating B-mode image data of the body tissue by using one of the plurality of received signals.

Configuration 6

The ultrasonic therapeutic apparatus according to Configuration 5, wherein the control unit is configured to cause the display device to display a sonicated-region image based on the sonicated-region data and a B-mode image based on the B-mode image data.

Configuration 7

The ultrasonic therapeutic apparatus according to Configuration 5, wherein the control unit is configured to cause the display device to display in a superimposed manner the sonicated-region image based on the sonicated-region data and the B-mode image based on the B-mode image data.

REFERENCE SIGNS LIST

2 transceiver unit, 3 center axis, 4 concavity, 10 HIFU transducer unit, 14 HIFU drive circuit, 16 ultrasonic probe, 18 transceiver circuit, 20 imaging computation unit, 22 controller, 24 display device, 26 drive device, 28 ultrasonic transducer, 30 control unit, 36 HIFU/imaging mixture wave, 38 therapeutic ultrasound, 40 trigger pulse, 42 heating burst, 44 therapeutic ultrasonic pulse, 46-1 first imaging pulse, 46-2 second imaging pulse, 46-3 third imaging pulse, 48 sonication pause period, 50-1 first interleaved pulse (auxiliary ultrasonic wave), 50-2 second interleaved pulse (auxiliary ultrasonic wave), 60 bubbles, 100 HIFU sonication apparatus (ultrasonic therapeutic apparatus).

The invention claimed is:

1. An ultrasonic therapeutic apparatus comprising:

an ultrasonic transducer for treatment;

an ultrasonic probe; and a control unit configured to control the ultrasonic transducer and the ultrasonic probe, wherein the control unit is configured to execute:

therapeutic ultrasound transmitting processing for causing the ultrasonic transducer to transmit a therapeutic ultrasonic wave;

auxiliary ultrasound transmitting processing for causing the ultrasonic transducer to transmit an auxiliary ultrasonic wave; and sonicated-region image generating processing for causing the ultrasonic probe to transmit a plurality of ultrasonic waves at different time points and with different phases after the therapeutic ultrasonic wave is transmitted, and combining a plurality of received signals based on a plurality of reflected ultrasonic waves that have been reflected by body tissue and received by the ultrasonic probe, to thereby generate sonicated-region data based on nonlinear components based on the respective received signals, and wherein the auxiliary ultrasound transmitting processing includes processing for causing the ultrasonic transducer to transmit the auxiliary ultrasonic wave at a time point between two time points at which two ultrasonic waves, of the plurality of ultrasonic waves generated by the sonicated-region image generating processing, that are adjacent to each other on a time axis are transmitted, the two ultrasonic waves serve as a source of the received signals to be combined in the sonicated-region image generating.

2. The ultrasonic therapeutic apparatus according to claim 1, wherein the auxiliary ultrasound transmitting processing includes processing for causing the ultrasonic transducer to transmit the auxiliary ultrasonic wave at a time point that is earlier than an intermediate time point between two time points at which two of the plurality of ultrasonic waves to be combined, that are adjacent to each other on a time axis are transmitted.

3. The ultrasonic therapeutic apparatus according to claim 2, wherein the intermediate time point is a time point corresponding to a midpoint between two points on the time axis.

4. The ultrasonic therapeutic apparatus according to claim 3, wherein each of the plurality of ultrasonic waves to be combined is followed by a plurality of auxiliary HIFU waves.

5. The ultrasonic therapeutic apparatus according to claim 1, wherein the auxiliary ultrasound transmitting processing includes processing for causing the ultrasonic transducer to transmit the auxiliary ultrasonic wave, after the therapeutic ultrasonic wave is transmitted, at a time point that is earlier than time points at which the plurality of ultrasonic waves of combination targets are transmitted.

6. The ultrasonic therapeutic apparatus according to claim 1, wherein the plurality of ultrasonic waves comprise M ultrasonic waves, and the plurality of received signals are signals based on the plurality of reflected ultrasonic waves received by the ultrasonic probe, based on the M ultrasonic waves of combination targets sequentially transmitted from the ultrasonic probe with a phase difference of 360°/M.

7. The ultrasonic therapeutic apparatus according to claim 1, wherein the control unit is configured to execute B-mode image generating processing for generating B-mode image data of the body tissue by using one of the plurality of received signals.

8. The ultrasonic therapeutic apparatus according to claim 7, wherein the control unit is configured to cause the display device to display a sonicated-region image based on the sonicated-region data and a B-mode image based on the B-mode image data.

9. The ultrasonic therapeutic apparatus according to claim 7, wherein the control unit is configured to cause the display device to display the sonicated-region image based on the sonicated-region data and the B-mode image based on the B-mode image data in a superimposed manner.

* * * * *